United States Patent
May et al.

(10) Patent No.: US 8,726,739 B2
(45) Date of Patent: May 20, 2014

(54) TORSIONAL SENSOR INCLUDING A HIGH-PRESSURE SEALING MECHANISM AND SYSTEM FOR MEASUREMENT OF FLUID PARAMETERS

(75) Inventors: Andrzej Michal May, Schenectady, NY (US); John Robert Ward, Tamworth (GB); Vamshi Krishna Reddy Kommareddy, Bangalore (IN)

(73) Assignee: General Electric Company, Niskayuna, NY (US)

( * ) Notice: Subject to any disclaimer, the term of this patent is extended or adjusted under 35 U.S.C. 154(b) by 232 days.

(21) Appl. No.: 13/281,684

(22) Filed: Oct. 26, 2011

(65) Prior Publication Data

US 2013/0104648 A1    May 2, 2013

(51) Int. Cl.
*G01F 1/66*    (2006.01)
*G01F 1/20*    (2006.01)

(52) U.S. Cl.
USPC ..................... 73/861.21; 73/861.18

(58) Field of Classification Search
USPC ....................... 73/861, 861.18–19, 861.21–26
See application file for complete search history.

(56) References Cited

U.S. PATENT DOCUMENTS

| | | | |
|---|---|---|---|
| 4,893,496 A | 1/1990 | Bau et al. | |
| 6,732,595 B2 | 5/2004 | Lynnworth | |
| 6,880,410 B2 | 4/2005 | Drahm et al. | |
| 6,912,918 B1 | 7/2005 | Lynnworth et al. | |
| 7,318,355 B2 | 1/2008 | Ishikawa | |
| 2002/0123256 A1* | 9/2002 | Brickett | 439/140 |
| 2006/0152011 A1* | 7/2006 | Fraenkel | 290/54 |
| 2011/0132103 A1 | 6/2011 | Gottlieb et al. | |
| 2011/0167906 A1* | 7/2011 | Goravar et al. | 73/32 A |

OTHER PUBLICATIONS

Rogers et al.,"Ultrasonic Level, Temperature, and Density Sensor", IEEE Transactions on Nuclear Science,vol. 29, Issue 1, pp. 665, Feb. 1982.

Kim et al.,"Torsional Sensor Applications in Two-Phase Fluids", IEEE transactions on Ultrasonics, Ferroelecrics, and Frequency control,vol. 40, Issue 5, pp. 563-576, Sep. 1993.

Shepard et al.,"Measurements of Density and Viscosity of One- and Two-Phase Fluids with Torsional Waveguides", IEEE Transactions on Ultrasonics, Ferroelectrics and Frequency Control,vol. 46, Issue 3,pp. 536-548, May 1999.

Visvanathan et al.,"Ultrasonic Torsional Guided Wave Sensor for Flow Front Monitoring Inside Molds", Review of Scientific Instruments,vol. 78, Issue 1, Jan. 2007.

* cited by examiner

*Primary Examiner* — Hezron E Williams
*Assistant Examiner* — David Z Huang
(74) *Attorney, Agent, or Firm* — Jason K. Klindtworth (57) ABSTRACT

A torsional sensor including a high-pressure sealing mechanism for sensing at least one parameter of a high-pressure fluid. The torsional sensor includes a torsional portion including a torsional rod sensor, a reference portion coupled to the torsional portion and including a transducer device and a high-pressure sealing mechanism coupled to the reference portion and the torsional portion and in sealing arrangement therewith. The high-pressure sealing mechanism is configured to provide for sealing therein the transducer device and allow for protrusion therethrough of a torsional rod sensor. At least a portion of the torsional sensor is mountable for immersion in the high-pressure fluid and operable to propagate a torsional wave that interacts with the high-pressure fluid along the at least portion of the torsional sensor so as to affect propagation of the torsional wave in a manner dependent on the at least one parameter of the high-pressure fluid.

24 Claims, 3 Drawing Sheets

TORSIONAL SENSOR INCLUDING A HIGH-PRESSURE SEALING MECHANISM AND SYSTEM FOR MEASUREMENT OF FLUID PARAMETERS

BACKGROUND

Embodiments presented herein relate generally to a torsional sensor including a high-pressure sealing mechanism used for measurement of at least one parameter of a high-pressure fluid by the propagation of torsional wave energy along the torsional sensor located at least partially in contact with the high-pressure fluid.

In industrial process control, it is often required to determine at least one parameter attributed to fluids along flow paths, for example in pipes. The parameters may include density of the fluid, fluid velocity, fluid level, temperature, fluid phase, or the like. There are a number of known sensors, which are used for detection of parameters associated with the fluids.

One such sensor used for detection of parameters associated with the fluids is a torsional sensor. In such a device, the torsional sensor is at least partially inserted into the fluid whose property needs to be measured. Wave energy is guided along the sensor held at least partially in contact with the fluid. The parameter of the fluid surrounding the torsional sensor influences the torsional wave characteristics, specifically the time of flight of the wave mode. In other words, the interaction of the guided wave energy along the sensor with the fluid results in a lower velocity of propagation of the guided wave energy along the sensor, so that the change in flight time of the wave, as compared to a reference time with the sensor in air or vacuum, provides an indication of a parameter of the fluid in contact with the sensor. In particular circumstances, where at least one of the fluid composition, container geometry and sensor characteristics are known, a measurement of flight time of the wave energy guided along the sensor may provide an indication of a parameter of the fluid. However, known torsional sensor designs are not suitable for operation in high-pressure environments, such as inside a high-pressure liquid pipeline at isostatic pressures of up to approximately 1380 bar. Previous attempts to design a high-pressure torsional sensor included forming a glass to metal seal around the torsional rod with the piezoelectric element on a low-pressures side of a mounting flange. This resulted in significant acoustic energy reflection from the glass to metal seal and reduced signal to noise ratio.

As a result, there is a continued need for an improved high-pressure torsional sensor and more specifically, a high-pressure torsional sensor that includes a high-pressure sealing mechanism to address the aforementioned and other shortcomings

BRIEF DESCRIPTION

In accordance with one exemplary embodiment, a torsional sensor for sensing at least one parameter of a high-pressure fluid is disclosed. The torsional sensor includes a reference portion, a torsional portion and a high pressure sealing mechanism. The reference portion includes a transducer. The torsional portion includes a torsional rod sensor coupled to the reference portion. The high-pressure sealing mechanism is coupled to the reference portion and in sealing arrangement therewith. The high-pressure sealing mechanism is further configured to provide for sealing therein the transducer device and allow for protrusion therethrough of the torsional rod sensor. The high-pressure sealing mechanism includes a high-pressure casing and a flexible seal. The high-pressure casing has contained therein a fluid. The high-pressure casing is configured to provide for equalization of the high-pressure fluid and the fluid contained within the high-pressure casing. The flexible seal is disposed about the torsional rod sensor and in sealing engagement with the high-pressure casing. The flexible seal is further configured to provide for passage therethrough of a torsional wave. At least a portion of the torsional sensor is mountable for immersion in the high-pressure fluid and operable to propagate a torsional wave that interacts with the high-pressure fluid along the at least portion of the torsional sensor so as to affect propagation of the torsional wave in a manner dependent on the at least one parameter of the high-pressure fluid.

In accordance with another exemplary embodiment, a torsional sensor for sensing at least one parameter of a high-pressure fluid is disclosed. The torsional sensor includes a reference portion, a high pressure seal, a torsional portion and a high-pressure sealing mechanism. The reference portion includes a transducer. The high-pressure seal is configured for mounting and sealing the transducer device within the reference portion. The torsional portion includes a torsional rod sensor coupled to the reference portion. The high-pressure sealing mechanism is coupled to the reference portion and in sealing arrangement therewith. The high-pressure sealing mechanism is configured to provide for sealing therein the transducer device and allow for protrusion therethrough of the torsional rod sensor. The high-pressure sealing mechanism including a high-pressure casing, a pressure equalizing mechanism and a flexible seal. The casing has contained therein a fluid. The pressure equalizing mechanism is configured to provide for equalization of the high-pressure fluid and the fluid contained within the casing. The flexible seal is disposed about the torsional rod sensor and in sealing engagement with the casing. The flexible seal is configured to provide for passage therethrough of a torsional wave. At least a portion of the torsional sensor is mountable for immersion in the high-pressure fluid and operable to propagate a torsional wave that interacts with the high-pressure fluid along the at least portion of the torsional sensor so as to affect propagation of the torsional wave in a manner dependent on the at least one parameter of the high-pressure fluid.

In accordance with another exemplary embodiment, a sensing system for sensing at least one parameter of a high-pressure fluid is disclosed. The sensing system includes a torsional sensor, an excitation device and a processor device. The torsional sensor includes a torsional portion, a reference portion and a high-pressure sealing mechanism. The torsion portion includes a torsional rod sensor. The reference portion is coupled to the torsional portion and includes a transducer device configured to provide torsional wave excitation to the torsional sensor and detect wave energy from the torsional portion. The high pressure sealing mechanism is coupled to the reference portion and in sealing arrangement therewith. The high-pressure sealing mechanism is configured to provide for sealing therein the transducer device and allow for protrusion therethrough of the torsional rod sensor. The excitation device is configured to excite a torsional wave energy in the torsional sensor. At least a portion of the torsional sensor is mountable for immersion in the high-pressure fluid and operable to propagate the wave energy that interacts with the high-pressure fluid along the at least portion of the torsional rod sensor so as to affect propagation of the wave energy in a manner dependent on the at least one parameter of the high-pressure fluid. The processor device is configured to determine at least one parameter of the high-pressure fluid in response to an output from the transducer device.

In accordance with another exemplary embodiment, a method for sensing at least one parameter of a high pressure fluid is disclosed. The method including exciting a wave energy in a torsional sensor partially immersed in the high-pressure fluid via an excitation device so as to propagate the wave energy that interacts with the high-pressure fluid along at least a portion of the torsional sensor so as to affect propagation of the wave energy in a manner dependent on the at least one parameter of the high-pressure fluid, providing torsional excitation to the torsional sensor and detecting wave energy from the torsional portion via a transducer device and determining at least one parameter of the high-pressure fluid in response to an output from the transducer device. The torsional sensor includes a torsional portion, a reference portion and a high-pressure sealing mechanism. The torsional portion including a torsional rod sensor. The reference portion is coupled to the torsional portion and includes a transducer device configured to provide torsional excitation to the torsional sensor and detect wave energy from the torsional portion. The high-pressure sealing mechanism is coupled to the reference portion and in sealing arrangement therewith. The high-pressure sealing mechanism is configured to provide for sealing therein the transducer device and allow for protrusion therethrough of the torsional rod sensor.

DRAWINGS

The above and other aspects, features, and advantages of the present disclosure will become more apparent in light of the subsequent detailed description when taken in conjunction with the accompanying drawings in which.

DETAILED DESCRIPTION

As discussed herein below, embodiments presented disclose a torsional sensor for sensing at least one parameter of a high-pressure fluid. The torsional sensor includes a reference portion, a torsional portion coupled to the reference portion and a high-pressure sealing mechanism coupled to the reference portion and in sealing arrangement therewith. The high-pressure sealing mechanism is configured to provide for sealing therein the transducer device and allow for protrusion therethrough of the torsional rod sensor. At least a portion of the torsional sensor is mountable for immersion in the high-pressure fluid and operable to propagate a torsional wave that interacts with the high-pressure fluid along the at least portion of the torsional sensor so as to affect propagation of the torsional wave in a manner dependent on the at least one parameter of the high-pressure fluid. The at least one parameter include absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the high-pressure fluid. The high-pressure fluid may include a single-phase fluid, or a two-phase fluid mixture, or a multi-phase fluid and gas mixture. In a specific embodiment, a system incorporating the torsional sensor is disclosed. The exemplary torsional sensor design enables the operation of a torsional wave ultrasound transducer inside a high-pressure fluid conduit or vessel at isostatic pressures from 1 bar to approximately 1380 bar for measurement of at least one parameter of the high-pressure fluid. It should be understood that while the torsional sensor has been described herein as operable to sense at least one parameter of a high-pressure fluid from 1 bar approximately 1380 bar, it is anticipated that the described torsional sensor may be capable of sensing at least one parameter of a high-pressure fluid of greater than 1380 bar.

Figure 1:
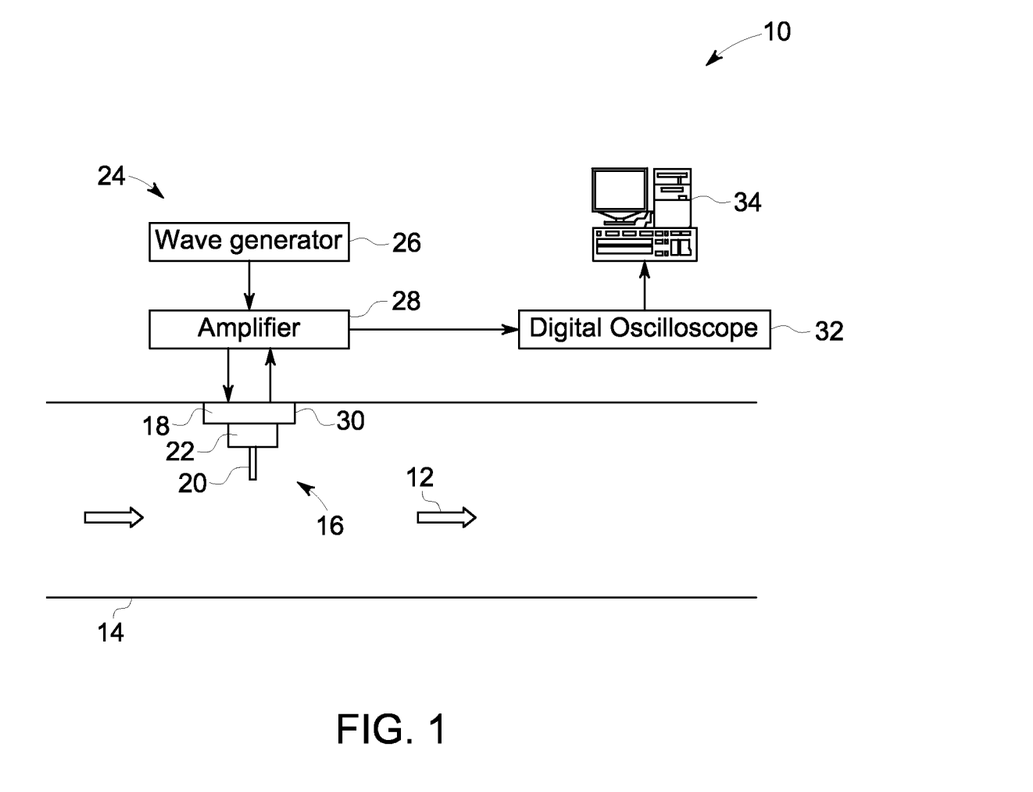
FIG. 1 is a block diagram of a sensing system for sensing at least one parameter of a high-pressure fluid flowing through a conduit in accordance with an exemplary embodiment.

Referring to FIG. 1, a block diagram of a high-pressure environment sensing system 10 for sensing at least one parameter of a high-pressure fluid 12 flowing through a conduit 14 is illustrated. In the illustrated embodiment and subsequent embodiments, the conduit 14 may be a vertical arrangement or a horizontal arrangement. It should be noted that even though a conduit is disclosed, the sensing system 10 is applicable to any device containing a high-pressure fluid for sensing at least one parameter attributed to the high-pressure fluid in both static and flowing conditions. The system 10 includes a torsional sensor 16 at least partially immersed in the high-pressure fluid 12 flowing through the conduit 14. The torsional sensor 16 includes a reference portion 18, a torsional portion 20 and a high-pressure sealing mechanism 22. The depth of the torsional sensor 16 immersed in the high-pressure fluid 12 may be varied.

The system 10 further includes an excitation device 24 having a wave generator 26 configured to transmit torsional wave energy via an amplifier 28 to the torsional sensor 16. In an exemplary embodiment, the torsional sensor 16 includes a transducer device 30 configured to provide torsional excitation to the torsional sensor 16. The ultrasonic guided wave, which propagates along the torsional sensor 16, detects the presence and nature of the surrounding high-pressure fluid 12. When the torsional sensor 16 is at least partially immersed in the high-pressure fluid 12, the propagation of wave is affected by at least one parameter of the high-pressure fluid 12. Hence at least one parameter of the high-pressure fluid 12 can be measured by detecting the propagation of wave energy along the sensor 16. At least one parameter includes absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the high-pressure fluid 12. The high-pressure fluid 12 may include a single-phase fluid, or a two-phase fluid mixture, or a multi-phase fluid and gas mixture. The excitation source and receiver may be, piezoelectric, curved piezoelectric, phased array magnetostrictive, laser-based electromagnetic acoustic transducer (EMAT), phased EMAT and membrane. The application of the exemplary sensor 16 to all such types of high-pressure fluid is contemplated.

In the illustrated embodiment, the transducer device 30 is also configured to detect the wave energy from the torsional portion 20 of the sensor 16. A corresponding output signal from the transducer device 30 may be fed via a digital oscilloscope 32 to a processor device 34, for example, a computer. In an alternative embodiment, an output analog signal from the transducer device 30 may be fed via a digital converter to a processor device. In addition, in an alternative embodiment, the output signals may be fed to a field programmable gate array. The processor device 34 is configured to determine at least one parameter of the high-pressure fluid 12 in response to the output signal from the transducer device 30. It should be noted herein that the configuration of the sensing system 10 is an exemplary embodiment and should not be construed in any way as limiting. The exemplary sensor 16 is applicable to any application requiring detection of at least one parameter attributed to the high-pressure fluid 12 in which the high-pressure fluid is contained in a vessel or flowing through a conduit. Typical examples include petroleum industry, oil & gas, or the like. The exemplary sensor design including the high-pressure sealing mechanism is explained in greater detail with reference to subsequent embodiments.

Figure 2:
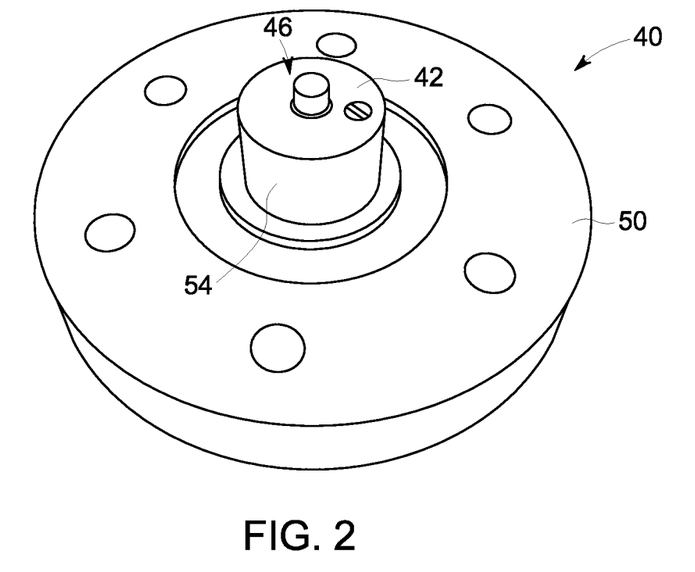
FIG. 2 is a perspective view of an exemplary torsional sensor including a high-pressure sealing mechanism in accordance with an exemplary embodiment.
Figure 3:
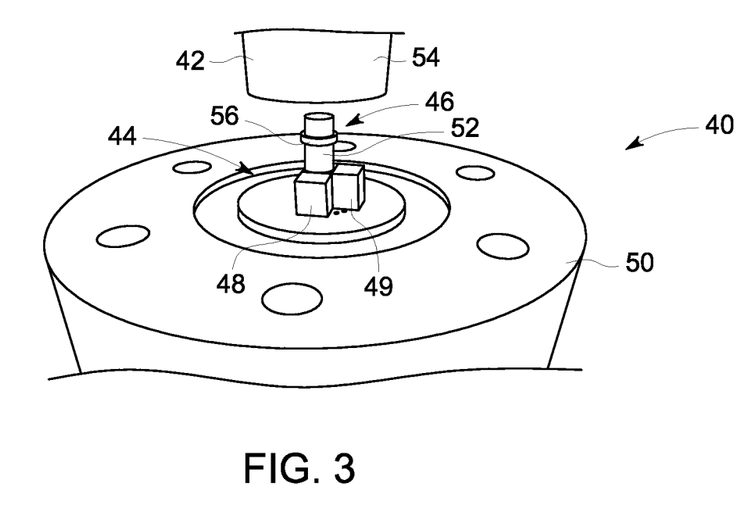
FIG. 3 is a perspective view of the exemplary torsional sensor in accordance with an exemplary embodiment, wherein the high-pressure sealing mechanism is illustrated prior to positioning relative to a reference portion and a torsional portion.

Referring to FIGS. 2-3, illustrated are perspective views of an exemplary torsional sensor 40. More specifically, illustrated in FIG. 2 is a perspective view of an exemplary torsional sensor 40 including a high-pressure sealing mechanism 42 positioned in sealing engagement with a reference portion 44 (FIG. 3) and a torsional portion 46 of the torsional sensor 40. Illustrated in FIG. 3 is a perspective view of the exemplary torsional sensor 40 wherein the high-pressure sealing mechanism 42 is illustrated prior to positioning relative to the reference portion 44 and the torsional portion 46.

In the illustrated embodiment, the torsional sensor 40 is shown mounted to a flange mounting 50. It should be noted that even though a flange mounting is disclosed onto which the torsional sensor 40 is mounted, alternate mounting configurations are anticipated, such as, but not limited to, mounting the torsional sensor directly onto a sidewall of a conduit or vessel containing a high-pressure fluid flow as described presently. The reference portion 44 includes a transducer device mounted to a surface of a flange mounting 50. More specifically, in the illustrated embodiment, the torsional sensor 40 is configured as a through transmission mode of operation in which one transducer device 48 is used for generating torsional wave energy and another transducer device 49 is used for receiving torsional wave energy. In all the embodiments disclosed herein, each sensor may alternatively be configured as a pulse echo mode of operation in which the transducer device is used for both generating and receiving a torsional wave energy. The torsional portion 46 includes a torsional rod sensor 52 coupled to the reference portion 44. The high-pressure sealing mechanism 42 is coupled to the reference portion 44 and the torsional portion 46 and in sealing engagement therewith. In an exemplary embodiment the high-pressure sealing mechanism 42 may be welded to the flange mounting 50. When configured in sealing engagement, the high-pressure sealing mechanism 42 provides for sealing therein the transducer devices 48 and 49 and allows for protrusion therethrough of the torsional rod sensor 52. The high-pressure sealing mechanism 42 is generally comprised of a high-pressure casing 54 having contained therein a fluid (described presently). In an embodiment, the casing 54 may be configured to compress in response to the high-pressure exerted thereon from the high-pressure fluid. More specifically, in an attempt to equalize pressure between the high-pressure fluid flowing in the conduit or vessel into which the torsional sensor 40 is positioned and the fluid contained within the casing 54, the casing 54 may be comprised of a material that is designed to compress under the high-pressure influence. Other means for equalizing the pressure between the high-pressure fluid flow and fluid contained within the casing will be described presently.

The high-pressure sealing mechanism 42 is further comprised of a flexible seal 56 disposed about the torsional rod sensor 52 and in sealing engagement with the casing 54. The flexible seal 56 is configured to provide for passage therethrough of a torsional wave. In an embodiment, the flexible seal 56 is formed of a ring of elastomeric material, such as polytetrafluoroethylene (PTFE), in the form of one or more O-rings within a piston structure or surrounding a diaphragm. It should be noted that the low-pressure 56 seal may be formed of alternate materials, including, but not limited to elastomeric polymers.

Figure 4:
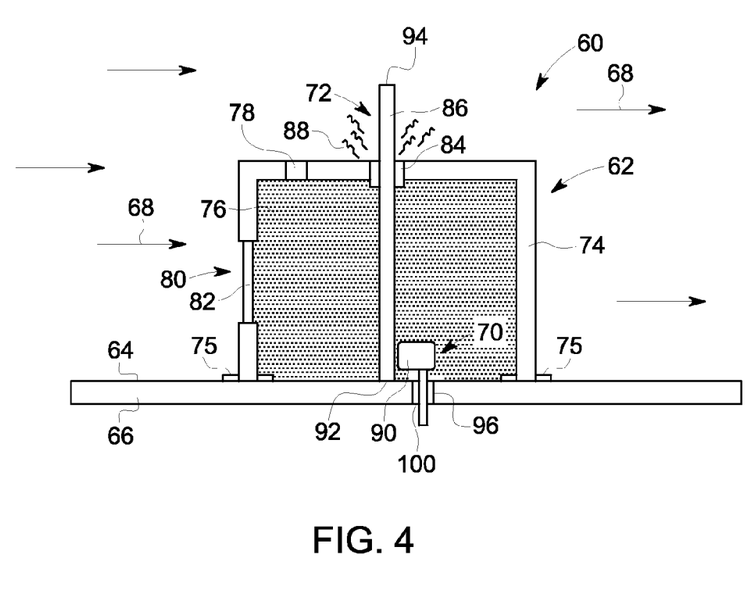
FIG. 4 is a sectional view of an exemplary torsional sensor in accordance with the exemplary embodiment disposed in a high-pressure fluid conduit.

Referring now to FIG. 4 illustrated in sectional view is an alternate embodiment of a torsional sensor 60 including a high pressure sealing mechanism 62. In this particular illustrated embodiment, the torsional sensor 60 is configured for sealing engagement on an interior surface 64 of a high pressure conduit 66 having a high-pressure fluid 68 flowing therethrough. Similar to the previously described embodiments, the torsional sensor 60 is designed for operation inside the conduit 66 at isostatic pressures from 1 bar to approximately 1380 bar. The torsional sensor 60 includes a reference portion 70, a torsional portion 72 and the high-pressure sealing mechanism 62. The high-pressure sealing mechanism 62 includes a high-pressure casing 74 sealably mounted to the interior surface 64 of the high pressure conduit 66 via a weld 75. The high-pressure casing 74 is configured to contain therein a fluid 76. Fluid 76 provides a medium that allows pressurization of the inside of the casing 74 with minimal change in volume (i.e. is highly incompressible, such as mineral oil). In an embodiment fluid 76 comprises at least one of an oil, grease, or other fluid capable of sufficient compression to equalize pressures as described presently. The casing 74 may further include a fluid fill port/plug 78 providing access to an interior of casing 74 and fluid 76. A pressure equalizing mechanism 80, such as a diaphragm 82, is configured to provide for equalization of the high-pressure fluid 68 and the fluid 76 contained within the casing 74. A flexible seal 84 is provided disposed about a torsional rod sensor 86 and in sealing engagement with the casing 74. The flexible seal 84 is configured to provide for passage therethrough of a torsional wave 88. At least a portion of the torsional sensor 60 is mountable for immersion in the high-pressure fluid 68 and operable to propagate the torsional wave 88 that interacts with the high-pressure fluid 68 along the torsional sensor 60 so as to affect propagation of the torsional wave 88 in a manner dependent on at least one parameter of the high-pressure fluid 68. The exemplary torsional sensor 60 is applicable for sensing at least one parameter of any single-phase high-pressure fluid, two-phase high-pressure fluid mixture, and multi-phase high-pressure fluid/gas mixture.

In an embodiment, during operation of torsional sensor 60, a piezoelectric element, and more particularly a transducer device 90 coupled to a base 92 of the torsional rod sensor 86, is excited with an approximately 100 kHz (or as suited to the torsional rod dimensions) tone burst waveform from a signal generator, generally similar to excitation device 24 of FIG. 1, positioned external to the conduit 66. The tone burst waveform creates a guided torsional ultrasonic wave 88 in the torsional rod sensor 86 that propagates towards a tip 94 of the torsional rod sensor 86. Subsequent to reaching the tip 94, the guided torsional ultrasonic wave 88 is reflected back toward the base 92 of the torsional rod sensor 86, where the transducer device 90, operating in a pulse echo mode of operation in which the transducer device 90 is used for both generating and receiving a torsional wave energy, converts received mechanical vibrations back into electrical signals that are recorded by a receiver portion of the transducer device 90. The density and viscosity of the high-pressure fluid 68 that surrounds the torsional rod sensor 86 changes the characteristics of the guided torsional ultrasonic wave 88, which are measured by an external data processor, generally similar to processor device 34 of FIG. 1, using the signals recorded by the transducer device 90.

The electrical connections between the piezoelectric element, and more particularly the transducer device 90 and the external excitation device pass, through a high-pressure seal 96, such as a glass to metal seal, that passes through an opening 100 formed in the conduit 66. The high-pressure seal 96 forms a primary pressure seal for the casing 74 of the high-pressure sealing mechanism 62, which allows the torsional sensor 60 to operate in a high-pressure environment.

When initially inserted into the high-pressure conduit 66, the fluid 76 located inside the high-pressure casing 74 is close to atmospheric pressure (1 bar) while the high-pressure fluid 68 inside the high-pressure conduit 66 is at a much high-pressure (from 1 bar approximately 1380 bar). In an embodiment, the pressure equalizing mechanism 80, in the form of the diaphragm 82, is positioned relative to the high-pressure casing 74 and provides equalization of the high-pressure fluid 68 and the fluid 76 contained within the casing 74. As previously stated, other means for equalizing the pressure between the high-pressure fluid 68 and the fluid 76 contained within the casing 74 are anticipated, such as forming the casing 74 of a compressible material. The inclusion of the pressure equalizing mechanism 80 provides transmission of pressure into the interior of the casing 74 upon pressurization, thereby compressing the fluid 76 inside the casing 74. The compression of the fluid 76 causes the pressure of the fluid 76 to increase until it is substantially equal to the pressure of the high-pressure fluid 68 in the high-pressure conduit 66. Thus, at equilibrium, the pressure difference across the flexible seal 84 is approximately zero, provided the pressure equalizing mechanism 80 has sufficient compliance to eliminate the initial pressure difference across the casing 74.

As the guided acoustic wave propagates from the base 92 of the torsional rod sensor 86 to the tip 94, it passes from the fluid-filled casing 74 to the fluid-filled conduit 66 through the flexible seal 84. The flexible seal 84 passes the acoustic torsional wave 88 with minimal attenuation or reflection while preventing the fluid 76 inside the casing 74 from becoming contaminated by the high-pressure fluid 68 in the conduit 66. This efficient coupling of acoustic energy into the high-pressure fluid 68 improves the signal-to-noise ratio of the measurement system and reduces the transmitter power required for operation. In addition, improved mechanical stability is achieved over a sensor incorporating a single seal device at a pressure barrier.

As discussed with reference to the embodiments described above, the torsional sensor including the high-pressure sealing mechanism utilizes change in speed of wave energy propagating along the torsional portion due to the presence of surrounding fluid medium to detect at least one parameter of the high-pressure fluid medium. As the torsional wave propagates through the torsional portion of the sensor, acceleration and deceleration of fluid surrounding the torsional portion occurs. Normal forces are exerted on the surface of the torsional portion, which in turn act on the surrounding fluid. The fluid motion surrounding the torsional portion is induced by the normal velocity component of velocity at a fluid-solid interface and also by the viscous drag of the surrounding fluid. As a result, the propagation of the wave energy is attributed to the inertial of the surrounding fluid. At least one parameter of the surrounding fluid medium can be detected by determining speed of propagating wave energy. It should additionally be noted that in the embodiments discussed herein, although only a single torsional sensor is illustrated for sensing at least one parameter of a high-pressure fluid, any number of sensors and the location of the sensors within a conduit, or vessel, should not be construed as limiting.

As discussed previously, the incorporation of a high-pressure sealing mechanism in the torsional sensor design enables the operation of a torsional wave ultrasound transducer inside a high-pressure fluid conduit or vessel at isostatic pressures from 1 bar of up to 1380 bar for measurement of at least one parameter of the high-pressure fluid.

While only certain features of the torsional sensor including a high-pressure sealing mechanism have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A torsional sensor for sensing at least one parameter of a high-pressure fluid in a conduit, the torsional sensor comprising:
   a reference portion comprising a transducer device;
   a torsional portion comprising a torsional rod sensor coupled to the reference portion;
   a high-pressure sealing mechanism coupled to the reference portion and the torsional portion and in sealing arrangement therewith, the high-pressure sealing mechanism configured to provide for sealing therein the transducer device and allow for protrusion therethrough of the torsional rod sensor, the high-pressure sealing mechanism comprising:
      a high-pressure casing having contained therein a fluid, the high-pressure casing configured to provide for equalization of the high-pressure fluid and the fluid contained within the high-pressure casing; and
      a flexible seal disposed about the torsional rod sensor and in sealing engagement with the high-pressure casing, the flexible seal configured to provide for passage therethrough of a torsional wave,
   wherein the reference portion and the torsional portion of the torsional sensor are mounted relative to the conduit for immersion in the high-pressure fluid and operable to propagate a torsional wave that interacts with the high-pressure fluid along the at least portion of the torsional sensor so as to affect propagation of the torsional wave in a manner dependent on the at least one parameter of the high-pressure fluid.

2. The torsional sensor of claim 1, wherein the torsional sensor is configured for sensing at least one parameter of a high-pressure fluid from 1 bar to 1380 bar.

3. The torsional sensor of claim 1, further including a high-pressure seal configured for mounting and sealing the transducer device within the reference portion.

4. The torsional sensor of claim 1, wherein the flexible seal is comprised of an elastomeric material.

5. The torsional sensor of claim 4, wherein the elastomeric material is comprised of polytetrafluoroethylene (PTFE).

6. The torsional sensor of claim 1, wherein the high-pressure casing is configured to compress in response to an exerted increase in pressure.

7. The torsional sensor of claim 1, wherein the high-pressure casing further includes a pressure equalizing mechanism configured to provide for equalization of the high-pressure fluid and the fluid contained within the high-pressure casing.

8. The torsional sensor of claim 7, wherein the pressure equalizing mechanism is a diaphragm.

9. The torsional sensor of claim 1, wherein the torsional sensor is configured for sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the high-pressure fluid.

10. The torsional sensor of claim 1, wherein the torsional sensor is configured for sensing at least one parameter of a single-phase fluid, a two-phase fluid mixture, or a multi-phase fluid mixture.

11. A torsional sensor for sensing at least one parameter of a high-pressure fluid in a conduit, the torsional sensor comprising:
a reference portion comprising a transducer;
a high-pressure seal configured for mounting and sealing the transducer device within the reference portion;
a torsional portion comprising a torsional rod sensor coupled to the reference portion; and
a high-pressure sealing mechanism coupled to the reference portion and the torsional portion and in sealing arrangement therewith, the high-pressure sealing mechanism configured to provide for sealing therein the transducer device and allow for protrusion therethrough of the torsional rod sensor, the high-pressure sealing mechanism comprising:
a casing having contained therein a fluid;
a pressure equalizing mechanism configured to provide for equalization of the high-pressure fluid and the fluid contained within the casing; and
a flexible seal disposed about the torsional rod sensor and in sealing engagement with the casing, the flexible seal configured to provide for passage therethrough of a torsional wave,
wherein the reference portion and the torsional portion of the torsional sensor are mounted relative to the conduit for immersion in the high-pressure fluid and operable to propagate a torsional wave that interacts with the high-pressure fluid along the at least portion of the torsional sensor so as to affect propagation of the torsional wave in a manner dependent on the at least one parameter of the high-pressure fluid.

12. The torsional sensor of claim 11, wherein the flexible seal is comprised of an elastomeric material.

13. The torsional sensor of claim 11, wherein the pressure equalizing mechanism is a diaphragm.

14. The torsional sensor of claim 11, wherein the torsional sensor is configured for sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the high-pressure fluid.

15. The torsional sensor of claim 11, wherein the torsional sensor is configured for sensing at least one parameter of a single-phase fluid, or a two-phase fluid mixture, or a multi-phase fluid mixture.

16. The torsional sensor of claim 11, wherein the torsional sensor is disposed in a high-pressure conduit having a high-pressure fluid flow therethrough from 1 bar to 1380 bar.

17. A sensing system for sensing at least one parameter of a high-pressure fluid in a conduit, the sensing system comprising:
a torsional sensor comprising a torsional portion comprising a torsional rod sensor, a reference portion coupled to the torsional portion and comprising a transducer device configured to provide torsional excitation to the torsional sensor and detect wave energy from the torsional portion and a high-pressure sealing mechanism coupled to the reference portion and the torsional portion and in sealing arrangement therewith, the high-pressure sealing mechanism configured to provide for sealing therein the transducer device and allow for protrusion therethrough of the torsional rod sensor;
an excitation device configured to excite a torsional wave energy in the torsional sensor, wherein the reference portion and the torsional portion of the torsional sensor are mounted relative to the conduit for immersion in the high-pressure fluid and operable to propagate the wave energy that interacts with the high-pressure fluid along the at least portion of the torsional rod sensor so as to affect propagation of the wave energy in a manner dependent on the at least one parameter of the high-pressure fluid; and
a processor device configured to determine at least one parameter of the high-pressure fluid in response to an output from the transducer device.

18. The sensing system of claim 17, wherein the high-pressure sealing mechanism comprises a high-pressure casing having contained therein a fluid and configured to provide for equalization of the high-pressure fluid and the fluid contained within the high-pressure casing and a flexible seal disposed about the torsional rod sensor and in sealing engagement with the high-pressure casing, the flexible seal configured to provide for passage therethrough of a torsional wave.

19. The sensing system of claim 17, wherein the torsional sensor is disposed proximate to an interior side of a wall of a high-pressure conduit.

20. The sensing system of claim 17, wherein the torsional sensor is configured to detect at least one parameter of a single-phase high-pressure fluid, or a two-phase high-pressure fluid mixture, or a multi-phase high-pressure fluid mixture.

21. The torsional sensor of claim 17, wherein the torsional sensor is configured for sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the high-pressure fluid.

22. A method for sensing at least one parameter of a high-pressure fluid in a conduit, the method comprising:
exciting a wave energy in a torsional sensor immersed in the high-pressure fluid via an excitation device so as to propagate the wave energy that interacts with the high-pressure fluid along at least a portion of the torsional sensor so as to affect propagation of the wave energy in a manner dependent on the at least one parameter of the high-pressure fluid, wherein the torsional sensor comprises a torsional portion mounted relative to the conduit for immersion in the high-pressure fluid and comprising a torsional rod sensor, a reference portion mounted relative to the conduit for immersion in the high-pressure fluid and coupled to the torsional portion and comprising a transducer device configured to provide torsional excitation to the torsional sensor and detect wave energy from the torsional portion and a high-pressure sealing mechanism coupled to the reference portion and the torsional portion and in sealing arrangement therewith, the high-pressure sealing mechanism configured to provide for sealing therein the transducer device and allow for protrusion therethrough of the torsional rod sensor, the high-pressure sealing mechanism including a high-pressure casing having contained therein a fluid and configured to provide for equalization of the high-pressure fluid and the fluid contained within the high-pressure casing and a flexible seal disposed about the torsional rod sensor and in sealing engagement with the high-pressure casing, the flexible seal configured to provide for passage therethrough of a torsional wave;

providing torsional excitation to the torsional sensor and detecting wave energy from the torsional portion via the transducer device;

determining at least one parameter of the high-pressure fluid in response to an output from the transducer device.

23. The method of claim 22, comprising sensing at least one parameter comprising absolute density, density profile, fluid level, absolute temperature, temperature profile, absolute viscosity, viscosity profile, absolute flow velocity, flow velocity profile, absolute fluid phase fraction, fluid phase fraction profile, or combinations thereof of the high-pressure fluid.

24. The method of claim 22, comprising sensing at least one parameter of a single-phase high-pressure fluid, or a two-phase high-pressure fluid mixture, or a multi-phase high-pressure fluid mixture.

\* \* \* \* \*

UNITED STATES PATENT AND TRADEMARK OFFICE
CERTIFICATE OF CORRECTION

PATENT NO. : 8,726,739 B2  
APPLICATION NO. : 13/281684  
DATED : May 20, 2014  
INVENTOR(S) : May et al.

Page 1 of 1

It is certified that error appears in the above-identified patent and that said Letters Patent is hereby corrected as shown below:

In the Specification

In Column 4, Line 12, delete "1 bar approximately" and insert -- 1 bar to approximately --, therefor.

In Column 7, Line 16, delete "1 bar approximately" and insert -- 1 bar to approximately --, therefor.

In Column 8, Lines 6-7, delete "pressures from 1 bar of up to" and insert -- pressures from 1 bar to --, therefor.

In the Claims

In Column 10, Line 34, in Claim 21, delete "torsional sensor of claim" and insert -- sensing system of claim --, therefor.

Signed and Sealed this  
Fourteenth Day of April, 2015

Michelle K. Lee  
*Director of the United States Patent and Trademark Office*